United States Patent
Robert et al.

(10) Patent No.: US 10,132,912 B2
(45) Date of Patent: Nov. 20, 2018

(54) METHOD AND APPARATUS FOR ESTIMATING REFLECTANCE PARAMETERS AND A POSITION OF A LIGHT SOURCE IN A SCENE

(71) Applicant: THOMSON LICENSING, Issy les Moulineaux (FR)

(72) Inventors: Philippe Robert, Rennes (FR); Salma Jiddi, Casablanca (MA); Matis Hudon, Rennes (FR)

(73) Assignee: Thomson Licensing, Issy le Moulineaux (FR)

( * ) Notice: Subject to any disclaimer, the term of this patent is extended or adjusted under 35 U.S.C. 154(b) by 0 days.

(21) Appl. No.: 15/268,584

(22) Filed: Sep. 17, 2016

(65) Prior Publication Data
US 2017/0082720 A1    Mar. 23, 2017

(30) Foreign Application Priority Data

Sep. 17, 2015 (EP) .................................... 15306453

(51) Int. Cl.
*G01B 11/14* (2006.01)
*G01S 3/783* (2006.01)
(Continued)

(52) U.S. Cl.
CPC ................. *G01S 3/783* (2013.01); *G01J 1/44* (2013.01); *G01N 21/4738* (2013.01); *G06T 7/70* (2017.01);
(Continued)

(58) Field of Classification Search
CPC . G01S 3/783; G06T 7/70; G06T 2207/10016; G06T 2207/10024;
(Continued)

(56) References Cited

U.S. PATENT DOCUMENTS 5,499,323 A    3/1996  Doi et al.

FOREIGN PATENT DOCUMENTS

| JP | 2007328460   | 12/2007 |
| KR | 20110092027  | 8/2011  |
| KR | 101342987    | 12/2013 |

OTHER PUBLICATIONS

"Lighting Estimation in Indoor Environments from Low-Quality Images", Oct. 7, 2012, ECCV 2012. Workshops and Demonstrations, Springer, Berlin, Heidelberg, pp. 380-389, ISBN: 978-3-642-33867-0, by Natalia et al.*

(Continued)

*Primary Examiner* — Jamil Ahmed
(74) *Attorney, Agent, or Firm* — Vincent E. Duffy

(57) ABSTRACT

A method, apparatus and system for estimating reflectance parameters and a position of the light source(s) of specular reflections of a scene include RGB sequence analysis with measured geometry in order to estimate specular reflectance parameters of an observed 3D scene. Embodiments include pixel-based image registration from which profiles of 3D scene points image intensities over the sequence are estimated. A profile is attached to a 3D point and to the set of pixels that display its intensity in the registered sequence. Subsequently, distinction is made between variable profiles that reveal specular effects and constant profiles that show diffuse reflections only. Then, for each variable profile diffuse reflectance is estimated and subtracted from the intensity profile to deduce the specular profile and the specular parameters are estimated for each observed 3D point. Then, the location of at least one light source responsible for the specular effects is estimated. Optionally, the parameters can be iteratively refined to determine color information and specular reflectance parameters.

20 Claims, 10 Drawing Sheets

(51) Int. Cl.
  *G01J 1/44* (2006.01)
  *G01N 21/47* (2006.01)
  *G06T 7/70* (2017.01)

(52) U.S. Cl.
  CPC .............. *G06T 2207/10016* (2013.01); *G06T 2207/10024* (2013.01); *G06T 2207/10028* (2013.01)

(58) Field of Classification Search
  CPC . G06T 2207/10028; G01J 1/44; G01N 21/47; G01N 21/4738
  See application file for complete search history.

(56) References Cited

OTHER PUBLICATIONS

Neverova et al., "Lighting Estimation in Indoor Environments from Low-Quality images", European Conference on Computer Vision, Florence, Italy, Oct. 7, 2012, pp. 380-389.

To et al., "Surface-Type Classification Using RGB-D", IEEE Transactions on Automation Science and Engineering, vol. 11, No. 2, Apr. 2014, pp. 359-366.

Lee et al., "Estimation of Intrinsic Image Sequences from Image+Depth Video", 12th European Conference on Computer Vision (ECCV 2012), Florence, Italy, Oct. 7, 2012, pp. 327-340.

Knecht et al., "Interactive BRDF Estimation for Mixed-Reality Applications", 20th International Conference on Computer Graphics, Visualization and Computer Vision (WSCG 2012), Plzen, Czech Republic, Jun. 26, 2012, pp. 47-56.

Jachnik et al., "Real-Time Surface Light-field Capture for Augmentation of Planar Specular Surfaces", 11th IEEE International Symposium on Mixed and Augmented Reality (ISMAR 2012), Atlanta, Georgia, USA, Nov. 5, 2012, pp. 91-97.

Phong, B. T., "Illumination for Computer Generated Pictures", Communications of ACM. vol. 18, No. 6, Jun. 1975, 311-317.

Hara et al., "Light Source Position and Reflectance Estimation from a Single View without the Distant Illumination Sssumption", IEEE Transactions on Pattern Analysis and Machine Intelligence, vol. 27, No. 4, Apr. 2005, pp. 493-505.

Li et al., "Reflectance and Light Source Position Estimation from a Sparse Set of Images", 2nd Workshop on Digital Media and Its Applications in Museum and Heritages, Chongqing, China, Dec. 10, 2007, pp. 106-111.

\* cited by examiner

METHOD AND APPARATUS FOR ESTIMATING REFLECTANCE PARAMETERS AND A POSITION OF A LIGHT SOURCE IN A SCENE

REFERENCE TO RELATED EUROPEAN APPLICATION

This application claims priority from European Application No. 15306453.0, entitled "Method and Apparatus for Estimating Reflectance Parameters and a Position of a Light Source In A Scene," filed on Sep. 17, 2015, the contents of which are hereby incorporated by reference in its entirety.

FIELD OF THE INVENTION

The present principles relate to image processing and more particularly, to a method and apparatus for estimating reflectance parameters and a position of at least one light source in a scene.

BACKGROUND OF THE INVENTION

Typically, image processing is based on the "appearance" of an object recorded on imaging elements by capturing an image. The appearance of the object is obtained by the imaging elements receiving light from the light source after being reflected at the object surface. Currently however, image processing also includes the processing of augmented reality images in which computer-generated graphics images, being virtual objects, are laid over a real image.

In such applications it is necessary to estimate the light source characteristics and reflectance properties of the object surfaces of a scene to be able to properly predict and apply expected reflections and shadows in a scene. It is also possible to modify the lighting positions and reflectance properties once the light source characteristics are known.

In current techniques for estimating light source characteristics and reflectance properties of a scene, a captured image of the light source, i.e., a light source image, is needed. In some instances such an image can be obtained in conjunction with the imaging of a scene and in other instances a separate image of the light source must be captured. In either case, it is essential to capture an image of the light source for estimating light source characteristics and reflectance properties of a scene.

However, what can be very useful is to be able to estimate light source characteristics and reflectance properties of a scene without the need to capture an image of the light source(s).

SUMMARY OF THE INVENTION

Embodiments of the present principles address the deficiencies of the prior art by providing a method and apparatus for estimating reflectance parameters and a position of at least one light source in a scene.

In one embodiment of the present principles, a method for estimating reflectance parameters and a position of at least one light source in a scene includes determining an intensity profile for a plurality of locations in the scene, separating constant intensity profiles from variable intensity profiles, estimating a diffuse reflectance component using the variable intensity profiles, deriving specular parameters from the diffuse component, determining a light source direction from the derived specular parameters and estimating a position of the at least one light source using at least one determined light source direction.

In an alternate embodiment of the present principles, an apparatus for estimating reflectance parameters and a position of at least one light source in a scene, includes a memory adapted to store control programs, instructions, content and data and a processor adapted to execute the control programs and instructions. Upon executing the control programs and instructions, the processor causes the apparatus to determine an intensity profile for a plurality of locations in the scene, separate constant intensity profiles from variable intensity profiles, estimate a diffuse reflectance component using the variable intensity profiles, derive specular parameters from the diffuse component, determine a light source direction from the derived specular parameters and estimate a position of the at least one light source using at least one determined light source direction.

BRIEF DESCRIPTION OF THE DRAWINGS

The teachings of the present principles can be readily understood by considering the following detailed description in conjunction with the accompanying drawings, in which.

DETAILED DESCRIPTION OF THE INVENTION

Figure 1:
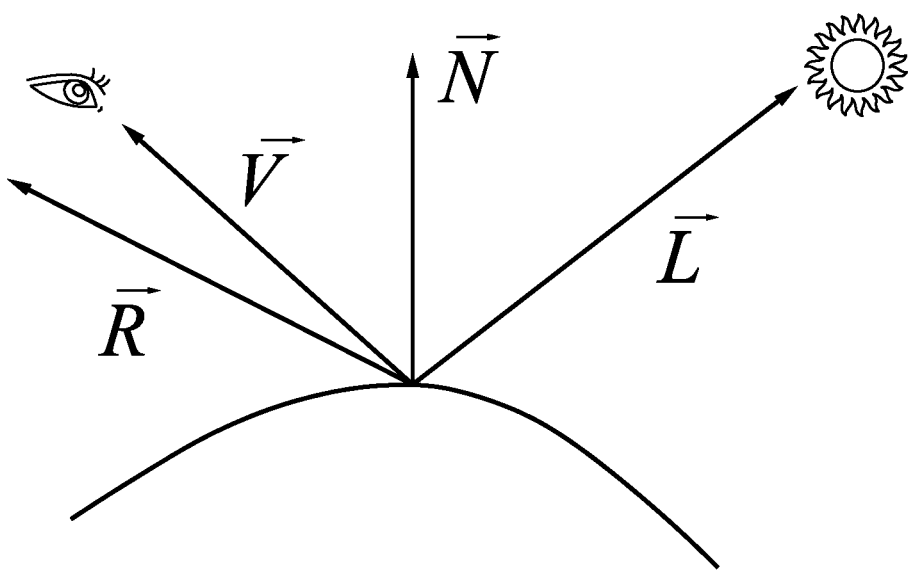
FIG. 1 depicts a graphical representation of the normalized vectors of specular reflection considering a particular point on a surface.

Embodiments of the present principles advantageously provide a method and apparatus for estimating reflectance parameters and a position of at least one light source in a scene using an RGBD sequence. Although the present principles will be described primarily within the context of resultant color variables associated with variable specular effects, the specific embodiments of the present principles should not be treated as limiting the scope of the invention. It will be appreciated by those skilled in the art and informed by the teachings of the present principles that the concepts of the present principles can be advantageously to color data as well as grey scale data.

The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), and non-volatile storage. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams, state transition diagrams, pseudocode, and the like represent various processes which may be substantially represented in computer readable media and so executed by a computer or processor, whether or not such computer or processor is explicitly shown.

Furthermore, because some of the constituent system components and methods depicted in the accompanying drawings can be implemented in software, the actual connections between the system components or the process function blocks may differ depending upon the manner in which the present principles are programmed. Given the teachings herein, one of ordinary skill in the pertinent art will be able to contemplate these and similar implementations or configurations of the present principles.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

Briefly, in accordance with various embodiments of the present principles, there is provided a method, apparatus and system for estimating diffuse and specular reflectance of the observed surfaces in, for example, a scene and for estimating a position of the light source(s) of specular reflections of the scene. Embodiments of the present principles are based on the acquisition of a sequence of RGB and Depth maps from a sensor (e.g. Kinect) moving in front of a scene of interest. In accordance with embodiments of the present principles, there is no other sensor dedicated to detect light sources and estimate their location. The sensor is used to observed the scene of interest and is not used to observe light sources. As such, embodiment of the present invention are able of estimating reflectance properties of the surfaces observed in the scene of interest and the light sources from RGB frames and depth maps showing the scene of interest.

In one embodiment of the present principles, variable specular effects produced by the light sources in a scene of interest are used to estimate a position of the light sources of the scene. That is, depending on the movement of a sensor detecting the scene, the location of the light sources, the orientation of the surfaces as well as their reflectance properties, some surface points can display a color that varies from frame to frame. Using such information, a color/intensity profile of the pixels of a reference frame is built. The profile describes the evolution of the color or intensity of the corresponding 3D points from frame to frame along the sequence. That is the location of the projection of the 3D point varies from frame to frame but as the depth map is available and the sensor pose is measured, the 3D point can be tracked from frame to frame and the intensity/color observed through the sensor frames is measured to create variable profiles. In accordance with the present principles, the information of the variable profiles is used to estimate the location of a light source(s) and the sepcular parameters of the corresponding 3D points (pixels of a reference frame).

Intrinsic image decomposition aims to separate an image into its reflectance and shading components. The reflectance component, R, contains the intrinsic color, or albedo, of surface points independent of the illumination environment. On the other hand, the shading component, S, consists of various lighting effects including shadows. The image, I, is considered as the product of these two (2) components as reflected in equation one (1), which follows:

$$I^p = R^p \cdot S^p \qquad (1)$$

in which p denotes a point in the image space. It should be noted that reflectance is supposed to be limited to a diffuse component. Therefore, in such cases a solution must be robust with respect to the presence of probable specular reflections.

There are known solutions for estimating reflectance parameters using an RGBD sequence (color+depth). In such solutions, a temporal filtering tends to implicitly isolate the diffuse components from the specular ones but then the specular effects are simply consigned to shading together with shadows. However, more precision is required to identify and analyze specular effects.

In addition, the decomposition in intrinsic images is extended to the explicit estimation of specular reflectance and specular lighting images. In this case, lighting characteristics are represented via the decomposition of the specular intensity map to obtain a specular lighting image. The latter image contains lighting information but also data intrinsic to the specular surfaces. Such solutions can be used for applications that do not need 3D light source location but is not sufficient if this location is required.

Even further, several solutions have been proposed to give account of the physical phenomena in the 3D scene. For example, the Phong reflection model describes the way a surface reflects light as a combination of the diffuse reflection of rough surfaces with the specular reflection of shiny surfaces according to equation two (2), which follows:

$$I^p = k_a i_a + \sum_m \left(k_d (\vec{L}_m \cdot \vec{N}) i_{m,d}\right) + \sum_m \left(k_s (\vec{R}_m \cdot \vec{V})^\alpha i_{m,s}\right) \qquad (2)$$

The first component of the addition on the right side relates to ambient lighting, the second one refers to diffuse lighting (the sum on m is applied to the number of light sources) and the third component refers to specular lighting. The parameters $k_a$, $k_d$ and $k_s$ are reflection coefficients, respectively ambient, diffuse (albedo) and specular. Parameter $\alpha$ refers to "shininess": the larger the value of the parameter, the more mirror-like it is.

FIG. 1 depicts a graphical representation of the normalized vectors of specular reflection considering a particular point on a surface. That is, considering a particular surface point, the normalized vectors $\vec{N}$, $\vec{L}$, $\vec{R}$, $\vec{V}$ refer respectively to the surface normal, the direction of a light source, the direction that a perfectly reflected ray of light would take from this point on the surface and the direction pointing towards the sensor. $\vec{R}$, $\vec{L}$ and $\vec{N}$ are linked by the relation according to equation three (3), which follows:

$$\vec{R} = 2(\vec{L} \cdot \vec{N})\vec{N} - \vec{L} \qquad (3)$$

It should be noted that the reflectance map, $R^p$, should not be confused with the direction parameter, $\vec{R}$.

In order to use such a model, the reflectance parameters of the object surfaces as well as the lighting sources have to be first estimated. Light sources are often identified via the direct observation of the light sources from a camera placed in the middle of the scene or via the observation of a light probe (also placed in the middle of the scene) that reflects the light sources. In addition, typically there should be at least two cameras in order to 3D locate the light sources via stereo (otherwise just the direction of the light sources is identified via a particular 3D point of the scene).

In existing solutions, a real-time surface light-field capture of planar specular surfaces via a hand-held camera has been proposed. Diffuse and specular reflection components are recovered without the need for probes or additional cameras. Practically, the hand-held moving camera captures the surface of a planar object under various view angles. From the multiple observations of a given 3D point, the diffuse component is extracted as the median value, and then the specular value is derived for each observation by subtracting the diffuse value from the observed color. The Phong equation, depicted in equation four (4) below, is used to describe the specular component $I_s^p$ of point as follows:

$$I_s^p = k_s(\vec{R} \cdot \vec{V})^\alpha i_s \qquad (4)$$

The observed surface is intended to be planar. Parameters $k_s$ and $\alpha$ are constant across the surface. Moreover, the light sources are supposed to be distant (the direction of the reflected light is supposed to be constant across the surface). A 4D light-field (corresponding to the specular component) of the planar surface is built from the various observations (2D position on the plane and 2D direction of observation). There is no estimation of the specular parameters.

In other existing solutions, a scene composed of different objects is considered. In such solutions, a RGBD Kinect sensor is used to observe the scene and a fish-eye camera captures the light sources. The Phong model is then used (without ambient lighting) as depicted in equation five (5), which follows:

$$I^p = \sum_m \left(k_d(\vec{L}_m \cdot \vec{N})i_{m,d}\right) + k_s(\vec{R} \cdot \vec{V})^\alpha i_s \qquad (5)$$

Each object is intended to have a unique set of reflectance parameters: $k_d$, $k_s$ and $\alpha$. These parameters are estimated for each object separately after segmentation by minimizing equation six (6), which follows:

$$E = \sum_P \left(I^p - \sum_m \left(k_d(\vec{L}_m \cdot \vec{N})i_{m,d}\right) - k_s(\vec{R}_m \cdot \vec{V})^\alpha i_s\right)^2 \qquad (6)$$

The above equation represents the square error, summed over all the pixels of a given object, between the pixel intensity and its Phong model decomposition.

In accordance with embodiments of the present principles, diffuse and specular surface reflectance are estimated from a RGB image sequence with known geometry. The geometry can have been estimated previously or can be captured on-line as a depth map together with the RGB frame via a RGB+depth sensor (e.g. Kinect sensor). In a static 3D scene, the RGBD sensor moves around the scene, such that the scene is observed under various view angles. A set of RGB and depth frames is acquired along the trajectory of the sensor. Camera pose with respect to a given coordinate system attached to the scene is available at each frame.

Using 3D geometry, surface normals can be computed and any occlusion of a surface by an object from a given 3D viewpoint can be estimated. Given a particular point of a surface in the scene, the corresponding image point in the frames of the video sequence can be located and can be classified as visible, occluded or out of field. Therefore, considering a frame of the input video sequence, it is possible to estimate a color profile of each pixel (as long as the point is visible from the viewpoint). In one embodiment, this profile comprises a triple curve that describes the evolution of the color of the corresponding 3D point in the scene through the set of viewpoints. A particular curve can be selected for each pixel. For example, in one embodiment the curve can be the 'green' curve or alternatively the curve can correspond to the sum of the three (3) color components possibly weighted according to one of the common formula used to convert color to luminance Using the Phong equation, the profile can be described according to equation seven (7), which follows:

$$I^p(t) = I_d^p + \sum_m \left(k_s(\vec{R}_m \cdot \vec{V}(t))^\alpha i_{m,s}\right) \qquad (7)$$

In equation seven (7), the variable 't' refers to the image index. Static ambient and diffuse components are grouped in the parameter $I_d^p$. In the specular component, parameters $k_s$ and $\alpha$ are peculiar to point P and temporally constant. Vector $\vec{R}_m$ is peculiar to both point P and light source m. Only $\vec{V}(t)$, the viewpoint vector of 3D point P at frame 't', can vary along the sequence. Therefore, the changes in the profile refer to the changes in specular effects. It should be noted that if the 3D point is not observed in view 't' the value is set to 'undetermined' and is not processed.

To estimate the reflectance parameters of the 3D points of the scene observed through the pixels of the reference image and the other registered images, the color/intensity profiles are examined. To be successful, viewpoints of the scene must be various enough to provide information exploitable for the estimation.

For each 3D point it is observed that, if the color/intensity profile is variable, the 3D point belongs to a specular surface. On the other hand, the profile can be constant for at least one of the following reasons:

The point is purely diffuse (no specular effect in spite of light sources that would create such effect if the surface was glossy)

The point is not submitted to specular effect (no light source that could create specular effect along the camera trajectory or presence of an object occluding these light sources)

Specular effect all along the sequence (due for example to a short trajectory and a wide light source)

Figure 2:
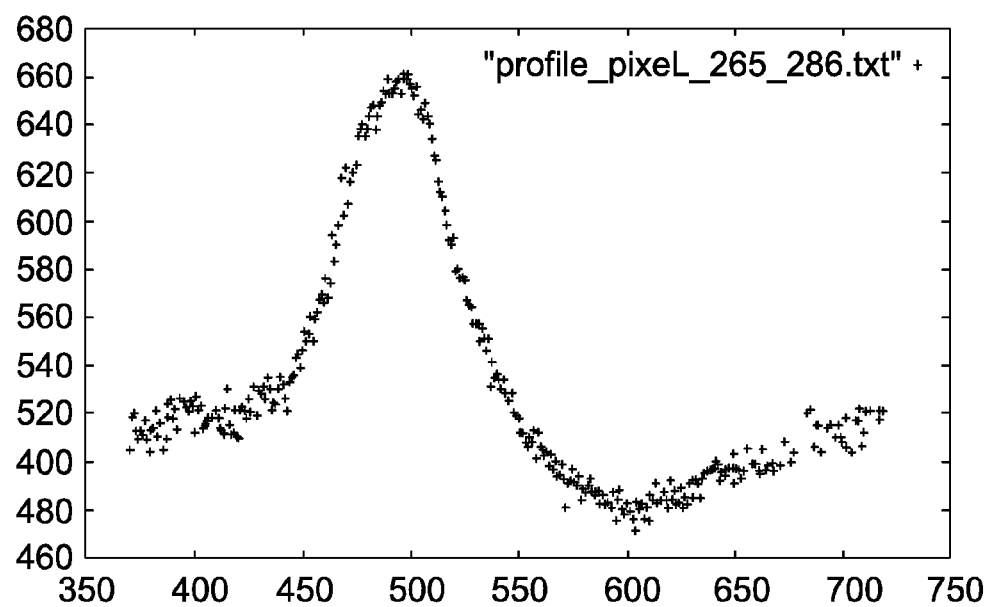
FIG. 2 depicts a graphical representation of a color/intensity profile containing specular effects.

FIG. 2 depicts a graphical representation of a color/intensity profile containing specular effects. The curve of FIG. 2 corresponds to the evolution of the sum of the three RGB color channels of a particular surface point throughout a set of different viewpoints of a scene. The abscissa (horizontal) axis corresponds to the frame number and the ordinate (vertical) axis corresponds to the sum of the three RGB color channels.

In accordance with embodiments of the present principles, the variable color/intensity profiles are separated from the constant color/intensity profiles. In order to better separate the variable profiles from the constant ones, a series of pre-processing steps are accomplished. Initially, for each pixel the number of frames in which the intensity information is missing is determined. If for more than half of the total number of frames the intensity information is missing, the profile information is not considered. In alternate embodiments of the present principles, other percentage other than less than 50% can be used. For the remaining profiles, a 1D Gaussian filter is applied in order to smooth the curve and obtain more exploitable information. Subsequently, a series of statistical information including at least one of a minimum, maximum, mean, median, variance and standard deviation for the intensity profile is determined.

Figure 3:
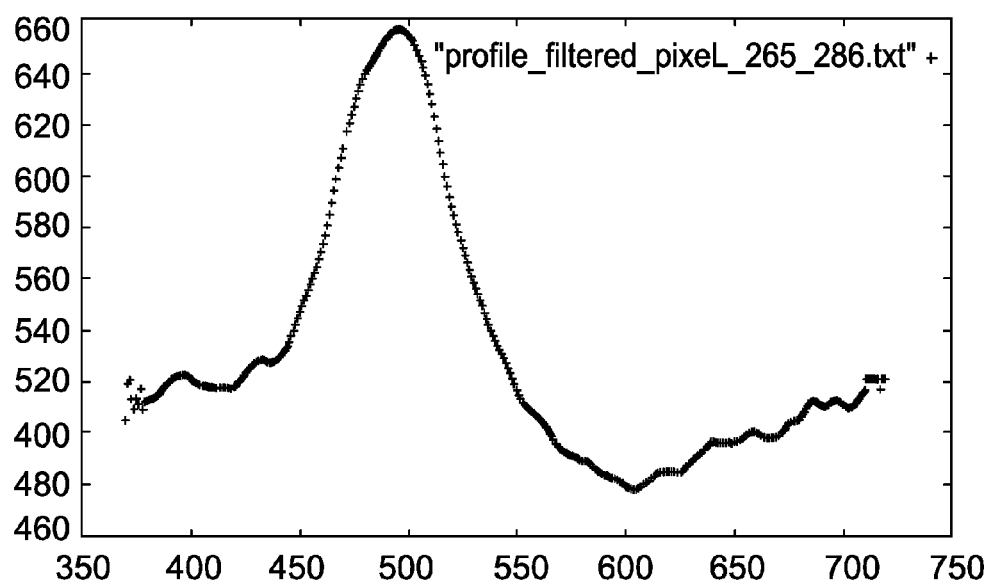
FIG. 3 depicts a graphical representation of the color/intensity profiles of FIG. 2 after filtering in accordance with an embodiment of the present principles.

FIG. 3 depicts a graphical representation of the color/intensity profiles of FIG. 2 after filtering in accordance with the present principles and as described above. As depicted in FIG. 3, the filtered profile of FIG. 2 provides a smoother curve having more discernable information. Using the information in FIG. 3, a threshold is chosen to classify a profile as being a constant profile or a variable profile. For example, in one embodiment of the present principles and referring profile of FIG. 3, if the absolute value of the difference between the median and the mean is found to be greater than a first threshold (e.g. Th1=10) or the standard deviation greater than another threshold (e.g. Th2=28), it is considered that the profile is a variable one. It should be noted that it is considered that the thresholds describe the fact that the pixel was under the impact of specular lighting during a set of viewpoints which made the difference between these statistics data noticeable. The intensity profiles below the thresholds are considered constant profiles. In various embodiments of the present principles, the thresholds are chosen to select all the points with specular effects. They can be chosen for example from a learning stage or first iteration. In case of overselection, the wrongly selected points will be able to be discarded in iterative steps.

Figure 4:
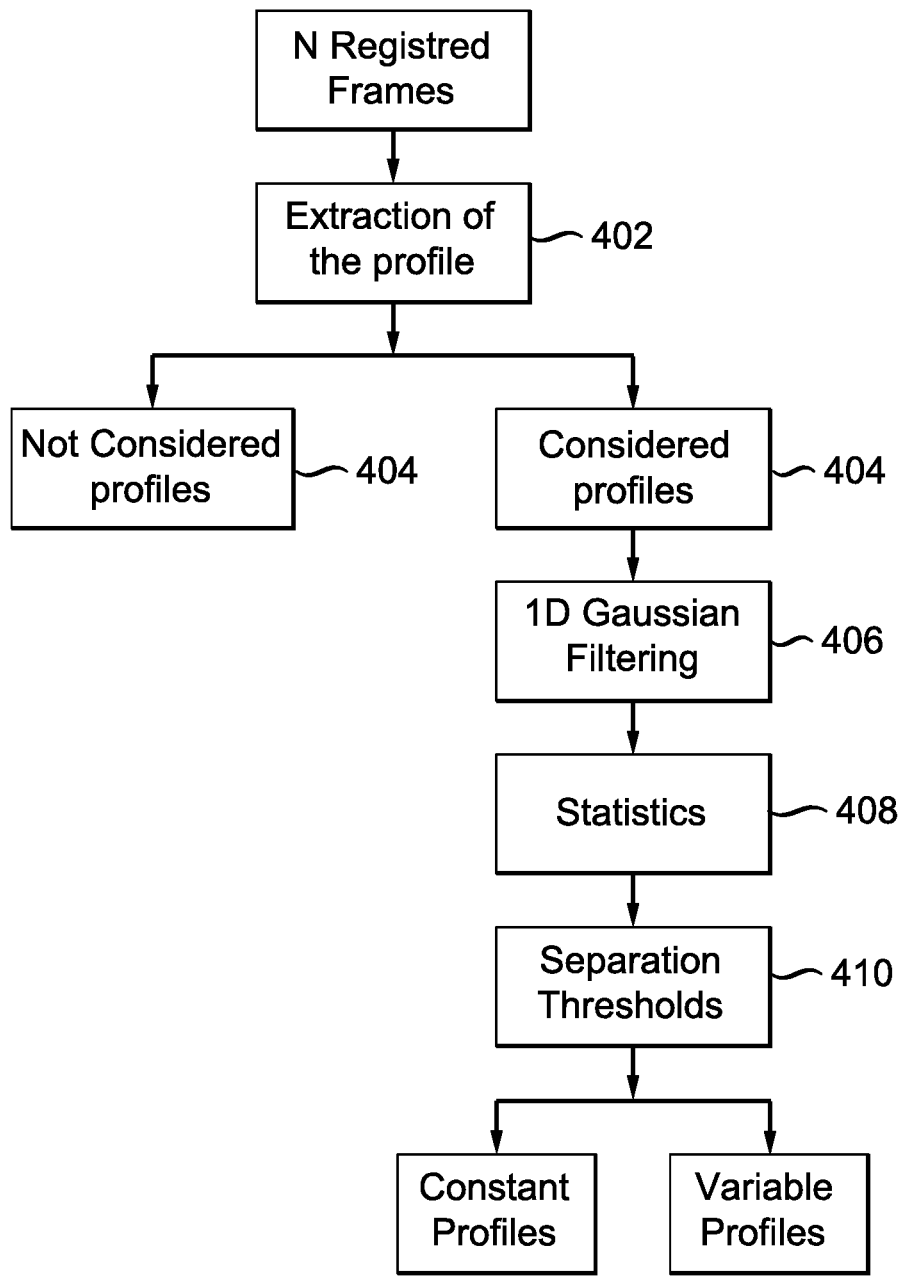
FIG. 4 depicts a flow diagram of a method for separating constant profiles from variable profiles in accordance with an embodiment of the present principles.

FIG. 4 depicts a flow diagram of a method for separating constant profiles from variable profiles in accordance with an embodiment of the present principles. The method 400 of FIG. 4 begins at step 402 during which, for N registered frames color/intensity profiles are extracted. As described above, in one embodiment of the present principles, in a static 3D scene, the RGBD sensor moves around the scene, such that the scene is observed under various view angles. A set of RGB and depth frames is acquired along the trajectory of the sensor. The method 400 can then proceed to step 404.

At step 404, it is determined if the color/intensity profiles should be considered or not. As described above, in one embodiment of the present principles, for each pixel the number of frames in which the intensity information is missing is determined. If for more than half of the total number of frames the intensity information is missing, the profile information is not considered. Nothing more is done with the profile information that is to be not considered. For the intensity profiles to be considered, the method 400 can then proceed to step 406.

At step 406, a filtering process is applied to a compilation of the color/intensity profiles to be considered. As described above, in one embodiment of the present principles, a 1D Gaussian filter is applied to the color/intensity profiles to be considered in order to smooth a curve resulting from a compilation of the color/intensity profiles to be considered in order to smooth the curve. The method 400 can then proceed to step 408.

At step 408, statistics of the filtered color/intensity profiles is determined. As described above, in one embodiment of the present principles a series of statistical information including at least one of a minimum, maximum, mean, median, variance and standard deviation for the intensity profiles is determined. The method 400 can then proceed to step 410.

At step 410, a threshold is chosen to classify a profile as being a constant profile or a variable profile. As described above, in one embodiment of the present principles, if the absolute value of the difference between the median and the mean is found to be greater than a first threshold (e.g. Th1=10) or if the standard deviation is greater than another threshold (e.g. Th2=28), it is considered that the profile is a variable one. The method 400 can then be exited.

For the pixels with a variable profile, it is assumed that the light sources are sparse and the 3D points are observed with only diffuse reflection in a significant number of views.

From the scene analysis and based on the previous results, the diffuse reflectance component $I_d^p$ for each pixel is equal to the minimum value of the variable and filtered profile. As such, an estimate of the color components for the diffuse reflectance are recovered as follows:

$I_d^p(\text{Red}) = \text{Red}(\text{Min}(I(t)))$ $I_d^p(\text{Green}) = \text{Green}(\text{Min}(I(t)))$ $I_d^p(\text{Blue}) = \text{Blue}(\text{Min}(I(t)))$ Then, the specular profile is derived from the diffuse component estimate $I_d^p$ according to equation eight (8), which follows:

$$I_s^p(t) = I^p(t) - I_d^p = \sum_m \left(k_s (\vec{R}_m \cdot \vec{V}(t))^\alpha i_{m,s}\right) \qquad (8)$$

As the light sources are considered sparse and modeled as point sources, just one light source creates the specular effect at a time. If the moving camera crosses a specular effect at a given 3D point along its trajectory, the profile of the point will be a lobe. But, if the trajectory is long, the profile may have more than one lobe. In accordance with the present principles, the lobes are separated at the minimal values between them. Then, in presence of one lobe, the profile is described by equation nine (9), which follows:

$$I_s^P(t) = k_s(\vec{R}_m \cdot \vec{V}(t))^\alpha i_{m,s} \qquad (9)$$

The unknown parameters are shininess α, 'mirror' direction of the light source $\vec{R}_m$ and specular reflectance combined with light intensity $k_s i_{m,s}$. Index m identifies the light source. In order to estimate the specular parameters of each profile, it is first assumed that there is only one source of lighting, then the specular parameters are estimated according to equation ten (10), which follows:

$$I_s^P(t) = k_s^P(\vec{R}_P \cdot \vec{V}_P(t))^\alpha i_s = k_s^P i_s (\cos \theta_P)^\alpha \qquad (10)$$

In equation ten (10) above, the constant $k_s^P i_s$ is equal to the maximum value of the intensity profile. Furthermore, since there is no guarantee that the profile has reached its maximum possible value, the estimation will be refined later in the estimation process according to equation eleven (11), which follows:

$$k_s^P i_s = \text{Max } I_s^P(t) \qquad (11)$$

When the pixel is at the maximum of the profile curve, the 'mirror' reflection corresponds to the viewpoint vector, $\vec{V}$, and can be determined according to equation twelve (12), which follows:

$$\vec{R}_P = \vec{V}_P \text{ when } I_s^P(t) = \text{Max } I_s^P(t) = k_s^P i_s \qquad (12)$$

The third parameter to estimate is "Shininess" $\alpha_p$ (p that refers to point P is missed in the equations for simplicity). This parameter is proper to each material and is known to be larger for surfaces that are smoother and more mirror-like. Mathematically speaking, the larger $\alpha_p$ is, the narrower the curve is. In one embodiment of the present principles, to estimate the "Shininess" parameter $\alpha_p$, the Nelder Mead Search (NMS) method is used as a minimization process. In such an embodiment, the direct search method is used because it can deal with nonlinear optimization problems for which derivatives may not be known and in the examples above, there exists a set of values with no guarantees of derivation or continuity. The method uses the concept of a simplex, which is a special polytope of n+1 vertices in n dimensions. Examples of simplices include a line segment on a line, a triangle on a plane, a tetrahedron in three-dimensional space and so forth. The direct search method approximates a local optimum of a problem with n variables with an objective function that varies smoothly.

In one embodiment of the present principles, an objective function which solves the minimization objective described above is represented according to equation thirteen (13), which follows:

$$F_P(\alpha) = \sum_t \left[ I_s^P(t) - k_s^P i_s (\vec{R}_P \cdot \vec{V}_P(t))^\alpha \right]^2 \qquad (13)$$

In this equation, the error between the observed specular intensity of point P in frame t, $I_s^P(t)$ and the intensity given by the Phong model in equation (10), is added over the whole selected specular profile of point P. The shininess parameter, $\alpha_p$, for which the objective function, $F_p(\alpha)$, has the least value will be kept as a best estimation.

Figure 5:
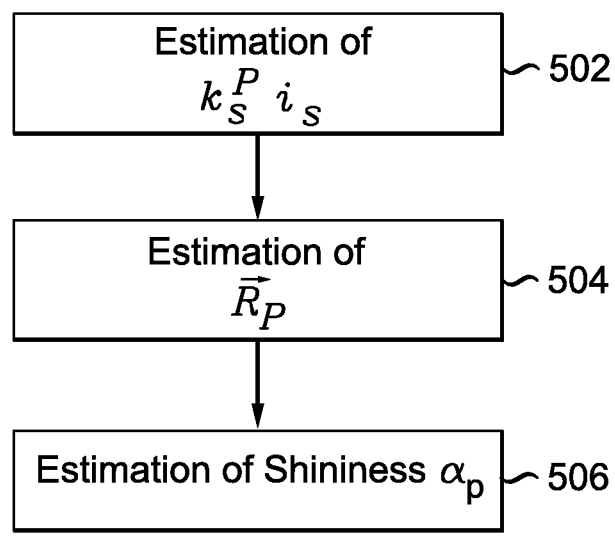
FIG. 5 depicts a flow diagram of a method for deriving specular parameters from the diffuse component in accordance with an embodiment of the present principles.

FIG. 5 depicts a flow diagram of a method for deriving specular parameters from the diffuse component in accordance with an embodiment of the present principles and as described above. The method 500 of FIG. 5 begins at step 502 during which a specular light intensity is estimated. For example and as described above, in one embodiment of the present invention, the constant $k_s^P i_s$ is equal to the maximum value of the intensity profile. The method 500 can then proceed to step 504.

At step 504, the mirror reflection is estimated. That is as described above and in one embodiment of the present principles, when a pixel is at the maximum of the profile curve, the 'mirror' reflection corresponds to the viewpoint vector and is determined according to equation twelve (12). The method 500 can then proceed to step 506.

At step 506, a shininess parameter is estimated. That is as described above and in one embodiment of the present principles, to estimate the "Shininess" parameter $\alpha_p$, the Nelder Mead Search (NMS) method is used as a minimization process. The method 500 can then be exited.

Having estimated the specular parameters of the scene as described above, the direction of a light source can be estimated. That is, because the 'mirror' reflection vector, $\vec{R}_P$, for each observed 3D point, P, with a variable profile is known, a corresponding light direction can be computed according to equation fourteen (14), which follows:

$$\vec{L}_P = 2 \cdot (\vec{R}_P \cdot \vec{N}_P) \cdot \vec{N}_P - \vec{R}_P \qquad (14)$$

Figure 6:
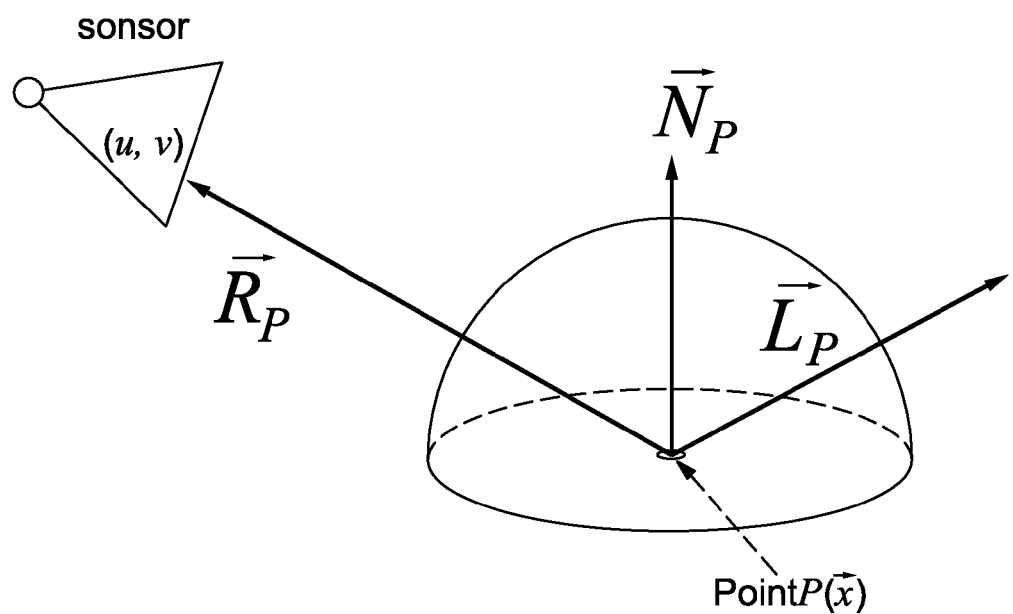
FIG. 6 depicts a graphical representation of normal and reflection light vectors of a point in accordance with an embodiment of the present principles.

FIG. 6 depicts a graphical representation of normal and reflection light vectors of a point, P. As depicted in FIG. 6 and as described above, because the 'mirror' reflection vector, $\vec{R}_P$, for a 3D point, P, is known, a corresponding light direction can be computed. That is, as depicted in FIG. 6, the normals $\vec{N}$ attached to the 3D points corresponding to the image pixels can be computed from the available geometry of the scene (e.g. depth frames).

In one embodiment of the present principles, to estimate the 3D position of the light source, the Nelder Mead Search method is used along with the following considerations:

the vector $\vec{S}$ that describes the 3D position of the light source, the vector $\vec{X}(P)$ of coordinates of the 3D points P that are subject to specular effect by the light source the direction of the light source for each of these 3D points: $\vec{L}(P)$.

In the embodiment described above, the objective is to estimate the vector $\vec{S}$ that maximizes the sum over the selected 3D points of scalar products between vectors ($\vec{S} - \vec{X}(P)$) and $\vec{L}(P)$ after normalization. This is equivalent to minimizing the sum over the selected 3D points of the angles between these vectors. In one embodiment of the present principles, an objective function which solves the minimization objective described above is represented according to equation fifteen (15), which follows:

$$F(\vec{S}) = \sum_P \left[ 1 - (\vec{S} - \vec{X}(P))_N \cdot \vec{L}(P)_N \right] \qquad (15)$$

Figure 7:
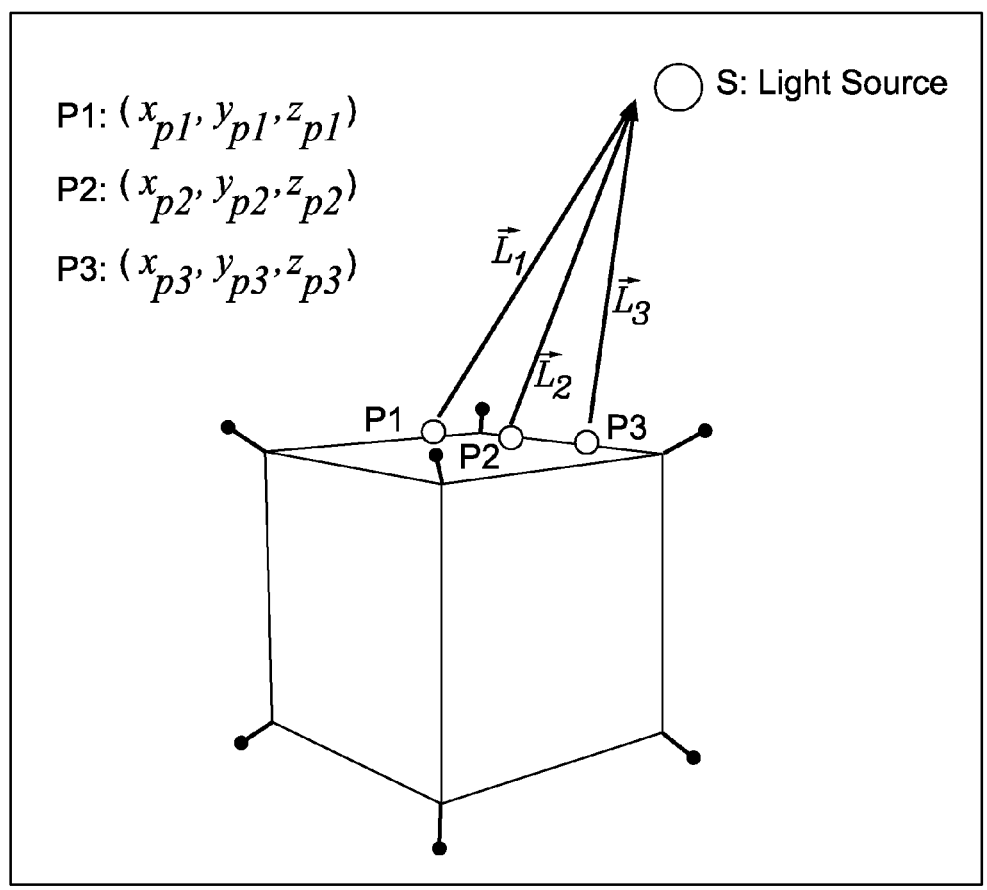
FIG. 7 depicts a pictorial representation of an estimation of a light source 3D position in accordance with an embodiment of the present principles.

In equation fifteen (15), the index, N, indicates that the vectors are normalized. FIG. 7 depicts a pictorial representation of an estimation of a light source 3D position in accordance with an embodiment of the present principles. As depicted in FIG. 7, the 3D position of a light source is estimated as described above and in accordance with embodiments of the present principles using three points in the scene.

Figure 8:
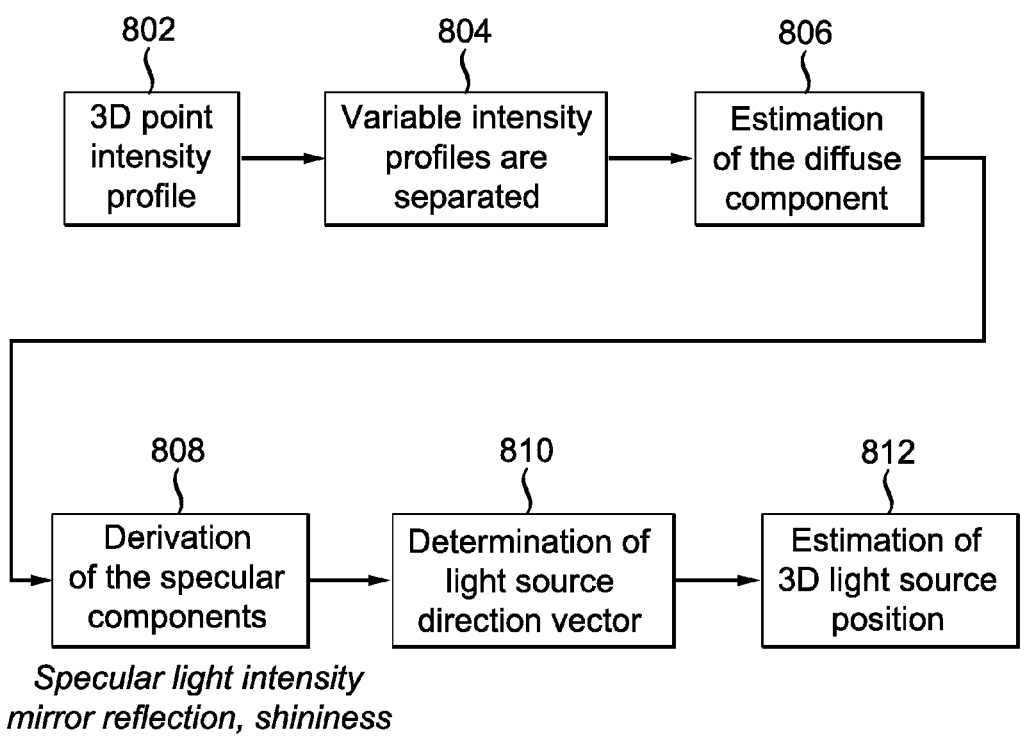
FIG. 8 depicts a flow diagram of a method for estimating a position of at least one light source in a scene in accordance with an embodiment of the present principles.

FIG. 8 depicts a flow diagram of a method for estimating a position of at least one light source in a scene in accordance with an embodiment of the present principles. The method 800 begins at step 802 during which an intensity profile for a plurality of locations in the scene is determined. For example, as described above, in one embodiment of the present principles an RGBD sensor moves around the scene, such that the scene is observed under various view angles. A set of RGB and depth frames is acquired along the trajectory of the sensor. Camera pose with respect to a given coordinate system attached to the scene is available at each frame. The method 800 can then proceed to step 804.

At step 804 constant intensity profiles are separated from variable intensity profiles. For example and as described above, in one embodiment of the present principles for each pixel of a sensor used to determine the intensity profiles a number of frames in which intensity information is missing is computed and the intensity information of an intensity profile having more than a threshold percentage of the intensity information missing is not considered. Subsequently a filter is applied to the remaining intensity profiles. Then at least a minimum intensity value, a maximum intensity value, a mean intensity value, a median intensity value, a variance of the intensity profile and a standard deviation of the intensity profile is determined and a threshold value is applied to the determined intensity values of at least one intensity profile to determine if an intensity profile is a variable profile or a constant profile. The method 800 can then proceed to step 806.

At step 806, a diffuse reflectance component is determined using the variable intensity profiles. For example and as described above, in one embodiment of the present principles, a diffuse reflectance component is considered equal to the minimum intensity value of a respective variable intensity profile and in various embodiments a diffuse reflectance component is estimated for each color component of the variable intensity profile. The method 800 can then proceed to step 808.

At step 808, specular parameters are derived using the diffuse component. For example and as described above, in one embodiment of the present principles, specular parameters such as specular light intensity, a mirror reflection vector, and a shininess component are derived for estimating a light direction vector of a light source. The method 800 can then proceed to step 810.

At step 810, a light direction vector is determined from the derived specular parameters. The method 800 can the proceed to step 812.

At step 812 a position of the at least one light source is estimated using at least the determined light direction vector. For example and as described above, in one embodiment of the present principles, the 3D position of a light source is estimated using three points in the scene as depicted in FIG. 7 above.

The method 800 can then be exited.

Optionally, in accordance with various embodiments of the present principles, the estimations determined above can be refined. Specifically, in one embodiment of the present principles this option leads to the refinement of the element $k_s^P i_s$ for each pixel P with a variable profile, the estimation of the light source color $\vec{T}_S$ and the specular reflectance $k_s^P$ of these pixels P. That is, as described above, in several embodiments of the present principles an estimation of the light source 3D position is based on the hypothesis that the maximum intensity value is available in a profile. However, since there is no guarantee that a profile hits its maximum during the sequence acquisition, a refinement step can be implemented to improve the parameter estimates in accordance with an embodiment of the present principles.

More specifically, because the position of each point in the camera's coordinate system and now an estimate of the light source position is known, the light direction vectors $\vec{L}(P)$ can be updated and, consequently, the value of the 'mirror' reflection vector, $\vec{R}(P)$, for each point, P, can be refined according to equations sixteen (16) and seventeen (17), which follow:

$$\vec{L}_P = \vec{S} - \vec{X}_P \qquad (16)$$

$$\vec{R}_P = 2 \cdot (\vec{L}_P \cdot \vec{N}_P) \cdot \vec{N}_P - \vec{L}_P \qquad (17)$$

It should be noted that in equations sixteen (16) and seventeen (17), above, vectors $\vec{A}(P)$ are noted as $\vec{A}_P$ and that index P refers to a particular point, P.

Using Phong's reflection model, $k_s^P i_s$ can be derived according to equation eighteen (18), which follows:

$$k_s^P i_s = \frac{\sum_t \frac{I_s^P(t)}{(\vec{R}_P \cdot \vec{V}_P(t))^\alpha}}{N_T^P} \qquad (18)$$

In equation eighteen (18) above, $N_T^P$ is the number of selected observations in the specular profile of point P. The observations can be limited by selecting only those which have values of $(\vec{R}_P \cdot \vec{V}_P(t))$ above a threshold, that is such that the angle between the 2 vectors is smaller than a threshold. In one embodiment of the present principles, a threshold value for $(\vec{R}_P \cdot \vec{V}_P(t))$ is cosinus of 30°. Moreover, a requirement is also that $(\vec{R}_P \cdot \vec{V}_P(t))$ must be different from zero. So in one embodiment of the present principles a second threshold set to 0.1 is introduced in the selection of observations.

In accordance with the present principles, the specular reflectance constant $k_s^P$ is derived from $k_s^P i_s$. That is, using the set of filtered variable profiles corresponding to the same light source, the color vector, $\vec{T}_S^P$, of the specular light source which has impacted each 3D point, P, can be determined More specifically, the color vector, $\vec{T}_S^P$, of the specular light source is equal to the difference between vectors corresponding to the maximum and minimum intensities. A mean color vector $\vec{T}_S$ can be derived from the set of specular color vectors $\vec{T}_S^P$. The latter set is limited to those vectors which corresponding vector, $\vec{T}^P$, (corresponding to the maximum intensity) has no saturated component (i.e., all color components below 255) and such that this maximum has a zero first derivative.

Subsequently, the intensity, $I_s$, can be derived from the light source color vector, $\vec{T}_S$, in one embodiment as the sum of the 3 color components, and the specular reflectance can be derived for each point, P, according to equation nineteen (19), which follows:

$$k_s^P = \frac{k_s^P i_s}{I_s} \qquad (19)$$

As previously described above, the value of expression $k_s^P i_s$ is computed using equation of Phong's reflection model as reflected above in equation eighteen (18).

Figure 9:
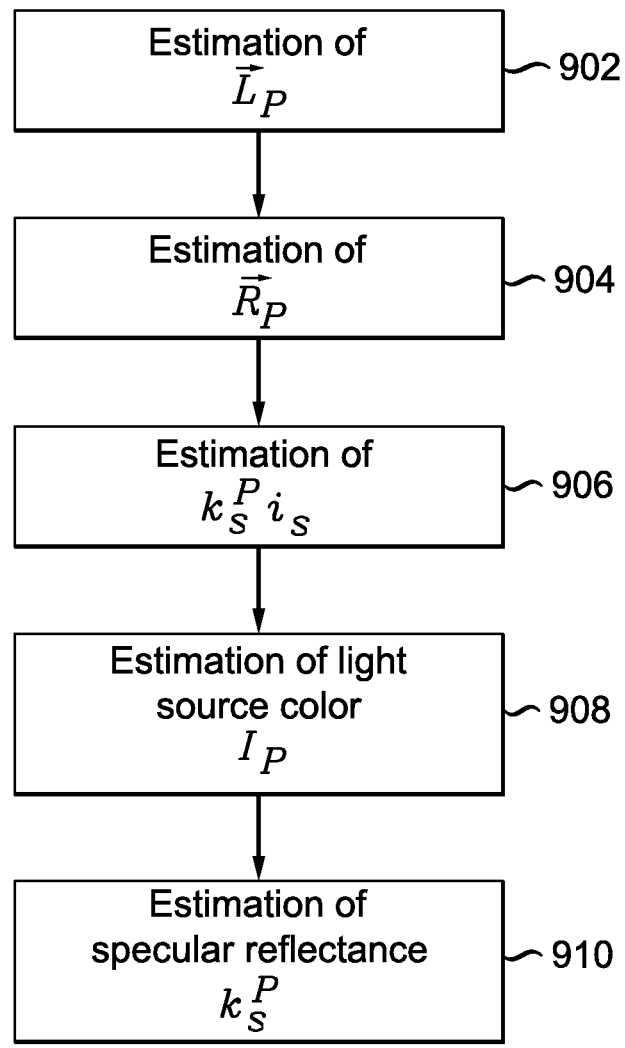
FIG. 9 depicts a flow diagram of a method for estimating a light source color and specular reflectance parameters in accordance with the refinement process described above in accordance with an embodiment of the present principles.

FIG. 9 depicts a flow diagram of a method for estimating a light source color and specular reflectance parameters in accordance with the refinement process described above in accordance with an embodiment of the present principles. The method 900 begins at step 902 during which because the position of each point in the camera's coordinate system and an estimate of the light source position is known, the light direction vectors $\vec{L}(P)$ are updated. The method 900 can then proceed to step 904.

At step 904, the value of the 'mirror' reflection vector, $\vec{R}(P)$, for each point, P, is refined. For example in one embodiment of the present principles and as described above, the mirror reflection vector is refined according to equations sixteen (16) and seventeen (17). The method 900 can then proceed to step 906.

At step 906, the specular light intensity is derived. For example in one embodiment of the present principles and as described above, the specular light intensity is derived according to using Phong's reflection model and equation eighteen (18). The method 900 can then proceed to step 908.

At step 908, the color vector, $\vec{T}_s^P$, of the specular light source which has impacted each 3D point, P, is determined. For example in one embodiment of the present principles and as described above, the color vector, $\vec{T}_s^P$, of the specular light source is equal to the difference between vectors corresponding to the maximum and minimum intensities. The method 900 can then proceed to step 910.

At step 910, the specular reflectance is derived. For example in one embodiment of the present principles and as described above, the specular reflectance can be derived for each point, P, according to equation nineteen (19).

The method 900 can then be exited.

Figure 10:
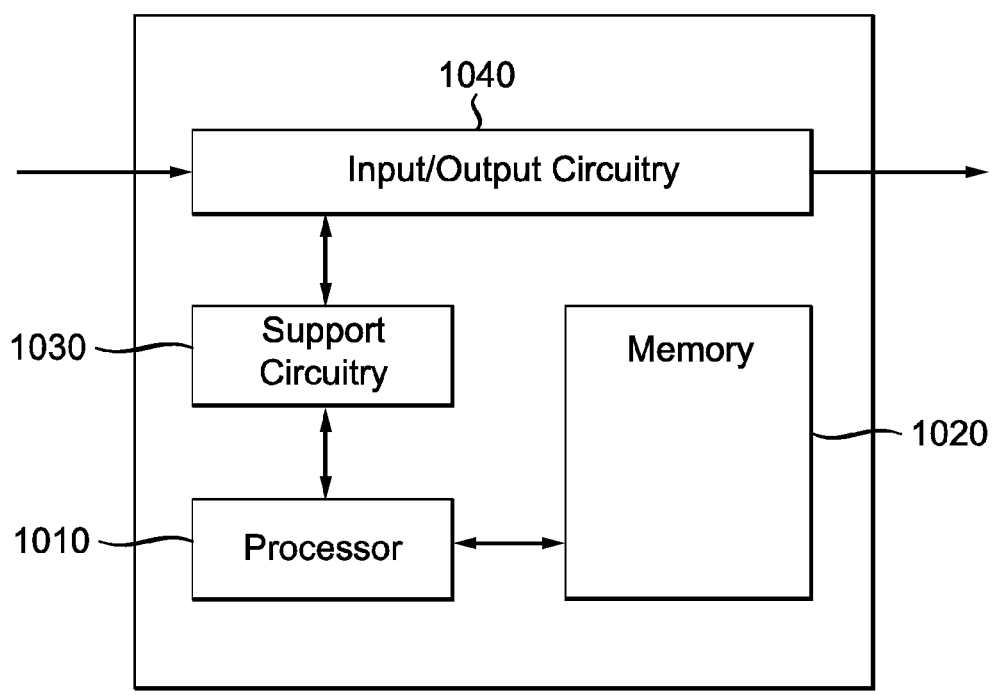
FIG. 10 depicts a high level block diagram of an apparatus for estimating reflectance parameters and a position of at least one light source in a scene using an RGBD sequence in accordance with an embodiment of the present principles.

FIG. 10 depicts a high level block diagram of an apparatus for estimating reflectance parameters and a position of at least one light source in a scene using an RGBD sequence in accordance with an embodiment of the present principles. The apparatus of FIG. 10 comprises a processor 1010 as well as a memory 1020 for storing control programs, instructions, software, video content, data and the like. The processor 1010 cooperates with conventional support circuitry 1030 such as power supplies, clock circuits, cache memory and the like as well as circuits that assist in executing the software routines stored in the memory 1020. As such, it is contemplated that some of the process steps discussed herein as software processes may be implemented within hardware, for example, as circuitry that cooperates with the processor 1010 to perform various steps. The apparatus of FIG. 10 also includes input-output circuitry 1040 that forms an interface between the various respective functional elements communicating with the apparatus.

Although the apparatus of FIG. 10 is depicted as a general purpose computer that is programmed to perform various control functions in accordance with the present principles, the invention can be implemented in hardware, for example, as an application specified integrated circuit (ASIC). As such, the process steps described herein are intended to be broadly interpreted as being equivalently performed by software, hardware, or a combination thereof.

Having described various embodiments of a method, apparatus and system for estimating reflectance parameters and a position of at least one light source in a scene using an RGBD sequence (which are intended to be illustrative and not limiting), it is noted that modifications and variations can be made by persons skilled in the art in light of the above teachings. It is therefore to be understood that changes may be made in the particular embodiments of the invention disclosed which are within the scope of the invention. While the forgoing is directed to various embodiments of the present principles, other and further embodiments of the invention may be devised without departing from the basic scope thereof.

The invention claimed is:

1. A method for estimating reflectance parameters and a position of at least one light source in a scene, from a sequence of RGB-D maps showing the scene, the method comprising:
   determining an intensity profile for a plurality of first locations in the scene, an intensity profile being the evolution of the intensity of a first location from map to map of said sequence and a first location being a three-dimension point determined according to pixels of said RGB-D maps;
   estimating, for second locations of said plurality of first locations having a variable intensity profile, a diffuse reflectance component according to said variable intensity profile;
   determining, for said second locations, a light source direction from specular parameters derived from the diffuse reflectance component; and
   estimating a position of the at least one light source using at least one determined light source direction.

2. The method of claim 1, further comprising:
   separating constant intensity profiles from variable intensity profiles,
   wherein said separating comprises:
   determining, for at least one of the intensity profiles, at least a minimum intensity value, a maximum intensity value, a mean intensity value, a median intensity value, a variance of the intensity profile and a standard deviation of the intensity profile;
   applying a threshold value to the determined intensity values of at least one intensity profile to determine if an intensity profile is a variable profile or a constant profile.

3. The method of claim 2, wherein applying a threshold value comprises:
   determining if the absolute value of a difference between a median intensity value and a mean intensity value of an intensity profile is greater than a threshold; and
   if the value of the difference is greater than the threshold, considering the intensity profile a variable intensity profile.

4. The method of claim 2, wherein applying a threshold value comprises:
   determining if a standard deviation of an intensity profile is greater than a threshold; and
   if the value of the standard deviation is greater than the threshold, considering the intensity profile a variable intensity profile.

5. The method of claim 1, wherein the diffuse reflectance component for a second location is equal to the minimum intensity value of a respective variable intensity profile.

6. The method of claim 5, wherein a diffuse reflectance component is estimated for each color component of the variable intensity profile.

7. The method of claim 1, wherein said specular parameters comprise at least one of a specular light intensity, a mirror reflection vector and a shininess component.

8. The method of claim 7, wherein for deriving the specular light intensity a maximum intensity value of a respective intensity profile is used.

9. The method of claim 8, wherein the mirror reflection vector is derived using a maximum specular light intensity value and is considered equal to a viewpoint vector.

10. The method of claim 7, wherein the shininess component is derived by applying a minimization function to known specular light intensity and mirror reflection values and using a result of the function that has a least value as a best estimate of the shininess component.

11. The method of claim 1, wherein the light source direction is determined, for said second locations, as a function of a mirror reflection vector and a normal vector at said second locations.

12. The method of claim 1, comprising:
updating the specular parameters and light source direction to determine a color vector and a specular reflectance parameter.

13. An apparatus for estimating reflectance parameters and a position of at least one light source in a scene, from a sequence of RGB-D maps showing the scene, the apparatus comprising:
a memory adapted to store control programs, instructions, content and data; and
a processor adapted to execute the control programs and instructions, said processor when executing said control programs causing said apparatus to:
determine an intensity profile for a plurality of first locations in the scene, an intensity profile being the evolution of the intensity of a first location from map to map of said sequence and a first location being a three-dimension point determined according to pixels of said RGB-D maps;
estimate, for second locations of said plurality of first locations having a variable intensity profile, a diffuse reflectance component according to said variable intensity profile;
determine, for said second locations, a light source direction from specular parameters derived from the diffuse reflectance component; and
estimate a position of the at least one light source using at least one determined light source direction.

14. The apparatus of claim 13, wherein the light source direction is determined, for said second locations, as a function of a mirror reflection vector and a normal vector at said second locations.

15. The apparatus of claim 13, wherein said processor further causing the apparatus to:
separate constant intensity profiles from variable intensity profiles, wherein said separating comprises:
determine, for at least one of the intensity profiles, at least a minimum intensity value, a maximum intensity value, a mean intensity value, a median intensity value, a variance of the intensity profile and a standard deviation of the intensity profile;
apply a threshold value to the determined intensity values of at least one intensity profile to determine if an intensity profile is a variable profile or a constant profile.

16. The apparatus of claim 15, wherein to apply a threshold value comprises:
determining if the absolute value of a difference between a median intensity value and a mean intensity value of an intensity profile is greater than a threshold; and
if the value of the difference is greater than the threshold, considering the intensity profile a variable intensity profile.

17. The apparatus of claim 15, wherein to apply a threshold value comprises:
determining if a standard deviation of an intensity profile is greater than a threshold; and
if the value of the standard deviation is greater than the threshold, considering the intensity profile a variable intensity profile.

18. The apparatus of claim 13, wherein the diffuse reflectance component for a second location is equal to the minimum intensity value of a respective variable intensity profile.

19. The apparatus of claim 18, wherein the diffuse reflectance component is estimated for each color component of the variable intensity profile.

20. The apparatus of claim 13, wherein said specular parameters comprise at least one of a specular light intensity, a mirror reflection vector and a shininess component.

* * * * *